US00RE38460E

(19) United States
(12) Reissued Patent
Zhu et al.

(10) Patent Number: US RE38,460 E
(45) Date of Reissued Patent: Mar. 9, 2004

(54) HUPERZINE A DERIVATIVES, THEIR PREPARATION AND THEIR USE

(75) Inventors: Dayuan Zhu, Shanghai (CN); Xican Tang, Shanghai (CN)

(73) Assignee: Shanghai Institute of Materia Medica Chinese Academy of Sciences, Shanghai (CN)

(21) Appl. No.: 09/799,127

(22) PCT Filed: Dec. 26, 1995

(86) PCT No.: PCT/CN95/00100

§ 371 (c)(1),
(2), (4) Date: Jun. 27, 1997

(87) PCT Pub. No.: WO96/20176

PCT Pub. Date: Jul. 4, 1996

Related U.S. Patent Documents

Reissue of:
(64) Patent No.: 5,929,084
Issued: Jul. 27, 1999
Appl. No.: 08/860,524
Filed: Jun. 27, 1997

(30) Foreign Application Priority Data

Dec. 28, 1994 (CN) ..... 94114057

(51) Int. Cl.[7] ..... A61K 31/349; A61K 31/44; C07D 221/06; C07D 221/22; A61P 25/28

(52) U.S. Cl. ..... 514/295; 546/93; 546/97

(58) Field of Search ..... 546/97, 93; 514/295

(56) References Cited

U.S. PATENT DOCUMENTS

| | | | |
|---|---|---|---|
| 4,929,731 | A | 5/1990 | Kozikowski et al. |
| 4,968,672 | A | 11/1990 | Jacobson et al. |
| 5,104,880 | A | 4/1992 | Kozikowski |
| 5,177,082 | A | 1/1993 | Yu et al. |
| 5,684,018 | A | 11/1997 | Alexander |

OTHER PUBLICATIONS

Liu et al., *Can. J. Chem*, 64(4):837–839 (1986).
Qian et al., *Tetrahedron Lett.*, 30(16):2089–90 (1989).
Tang et al., *Acta Pharmacologica Sinica*, 15(2):107–110 (1994) (Abstract Only).
Kozikowski et al., "Synthesis of Huperzine A and its Analogues and their Anticholinesterase Activity", *J. Org. Chem.*, 56:4636–4645 (1991).
Xiong et al., *Acta Pharmacologica Sinica*, 16(1):21–25 (1995).

*Primary Examiner*—Evelyn Mei Huang
(74) *Attorney, Agent, or Firm*—Burns Doane Swecker & Mathis, LLP

(57) ABSTRACT

The present invention relates to novel huperzine A derivatives of formula (II), wherein Y is or R" and Y together form =CH; R is ($C_1$–$C_5$) alkyl, wherein n is 0 or 1, X is H, ($C_1$–$C_5$) alkyl; ($C_1$–$C_5$) alkyloxy; nitro, halogen, carboxy, alkyloxycarbonyl, hydroxymethyl, hydroxy, amino substituted by bis-($C_1$–$C_5$) alkyl; —$(CH_2)_m$ COOZ, wherein m=0–5, Z is H or ($C_1$–$C_5$) alkyl; —CH=CH—G, wherein G is phenyl, furanyl, carboxy, alkyloxycarbonyl; and dihydro- or tetrahydro-pyridyl substituted by ($C_1$–$C_5$) alkyl at the nitrogen atom; R' is H, ($C_1$–$C_5$) alkyl, pyridoyl, benzoyl substituted by ($C_1$–$C_5$) alkyloxy; R" is H or ($C_1$–$C_5$) alkyl; processes for their use as acetylcholinesterase inhibitor.

(II)

24 Claims, No Drawings

HUPERZINE A DERIVATIVES, THEIR PREPARATION AND THEIR USE

Matter enclosed in heavy brackets [ ] appears in the original patent but forms no part of this reissue specification; matter printed in italics indicates the additions made by reissue.

This application is the national phase of PCT/CN95/00100, filed Dec. 26, 1995, published as WO96/20176 on Jul. 4, 1996.

The present invention relates to semi-synthesis of natural product, and particularly to alkaloid and analogues thereof.

In the past ten years a lot of researches have been made in foreign countries about application of choline esterase inhibitor to enhance the function of the intracerebral cholinergic system for the treatment of presenile dementia. Although delightful results of research have been obtained, there still exist some defects; at the time of producing the treatment effect, there occurs a relatively serious toxic side reaction; and the duration of the effect is relatively short.

In recent years China has isolated from a Chinese herb Lycopodium serratum Thunb., a new alkaloid huperzine A (5R, 9R, 11E)-5-amino-11-ethylidene-5,6,9,10-tetrahydro-7-methyl-5,9-methylene cycloocta [b] pyridyl-2(1H)-one having the formula (I)

(I)

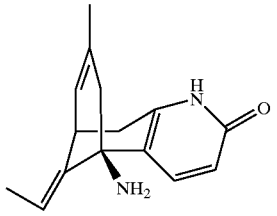

Upon a pharmacological study it is proved that it exhibits highly effective reversible anticholinesterase activity, and has selective inhibitory effect on intracerebral acetylcholinesterase (U.S. Pat. No. 5,177,082). In foreign countries modification of the structure of huperzine A has been carried out and analogues of huperzine A have been synthesized in hopes of discovering therefrom compounds having anticholinesterase activity [J. Org. Chem. 56, 1991(4636–4645)] and finding a method of synthesizing huperzine A [U.S. Pat. No. 4,929,731]. However, neither a good method nor an analogue having a better effect has been found so far.

The present invention has made use of the excellent resources of Chinese herbs in China to design a semi-synthesis starting from huperzine A, in the hope of finding among a great variety of huperzine A derivatives compounds having better treatment effect and lower toxicity than the existing huperzine A.

The present invention is carried out through the following steps:

1. Using alcohols such as ethanol as extraction solvent, from the plant Lycopodium serratum Thunb., the residue obtained is concentrated, and then treated with an inorganic acid (such as hydrochloric acid). The aqueous layer is neutralized with alkali (such as ammonia water, NaOH), after which an organic solvent (such as chloroform) is used to extract the total alkaloid. After the treatment, separation by layer chromatography is carried out to produce the compound of the formula (I).

2. After condensation is carried out between the compound of the formula (I), and the corresponding substituted aldehyde or the corresponding substituted acyl chloride or acid anhydride in anhydrous solvent, a compound of the formula (II) is obtained.

(II)

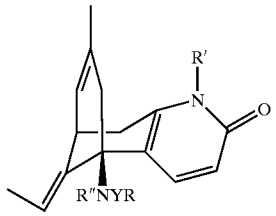

When Y is —C═O or —R", Y is ═CH, R is $C_1$–$C_5$ lower alkyl;

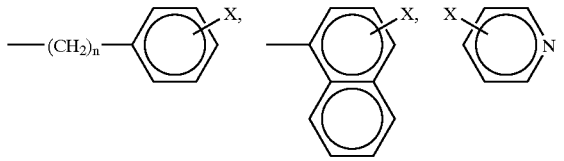

n=0,1, X is hydrogen, $C_1$–$C_5$ lower alkyl, $C_1$–$C_5$ lower alkyloxy, nitro, halogen, carboxy, alkyloxycarbonyl, hydroxymethyl, hydroxy, amino substituted by bis-$C_1$–$C_5$ lower alkyl; —$(CH_2)_m$ COOZ group, m=0–5, Z is hydrogen or $C_1$–$C_5$ lower alkyl; —CH═CH—G group, G is phenyl, furanyl, carboxy, alkyloxycarbonyl; dihydro or tetrahydropyridyl substituted by $C_1$–$C_5$ lower alkyl at the nitrogen atom;

R' is hydrogen, $C_1$–$C_5$ lower alkyl, pyridoyl, benzoyl substituted by $C_1$–$C_5$ lower alkyloxy;

R" is hydrogen and $C_1$–$C_5$ lower alkyl.

When Y is C═O, R is $C_1$–$C_5$ lower alkyl,

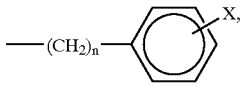

n=0,1, X is hydrogen, $C_1$–$C_5$ lower alkyloxy, carboxy, alkyloxycarbonyl, pyridyl, dihydro or tetrahydropyridyl substituted by $C_1$–$C_5$ lower alkyl at the nitrogen atom; —$(CH_2)_m$ COOZ group, m=0–5, Z is hydrogen or $C_1$–$C_5$ lower alkyl; —CH═CH—G group, G is phenyl, furanyl, carboxy, alkyloxycarbonyl;

R' is hydrogen, $C_1$–$C_5$ lower alkyl, pyridoyl, benzoyl substituted by $C_1$–$C_5$ lower alkyloxy;

R" is hydrogen and $C_{1-5}$ lower alkyl.

When R", Y are ═CH, R is

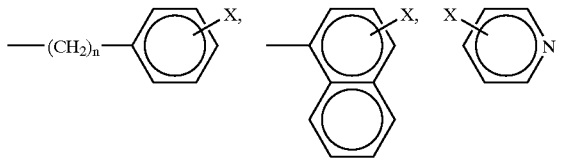

n=0, X is hydrogen, $C_1$–$C_5$ lower alkyl, $C_1$–$C_5$ lower alkyloxy, nitro, halogen, hydroxy, hydroxymethyl, amino substituted by bis-$C_1$–$C_5$ lower alkyl; —CH═CH—G group, G is phenyl, furanyl;

R' is hydrogen and $C_1$–$C_5$ lower alkyl.

Huperzine A derivatives:

| No. | Y | R | R' | R" |
|---|---|---|---|---|
| No. 1 | C═O | HOOC—$CH_2CH_2$— | H | H |
| No. 2 | C═O | $C_6H_5CH_2$— | H | H |
| No. 3 | C═O | 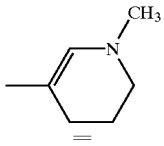 | $CH_3$ | $CH_3$ |
| No. 4 | C═O | 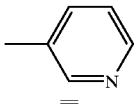 | H | H |
| No. 5 | C═O | 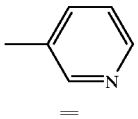 | 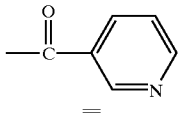 | H |
| No. 6 | C═O | 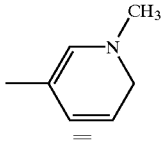 | H | H |
| No. 7 | C═O | 4-$CH_3OC_6H_4$— | H | H |
| No. 8 | C—O | 2,3,4-$(CH_3O)_3C_6H_2$— | H | H |
| No. 9 | C═O | 2,3,4-$(CH_3O)_3C_6H_2$— | 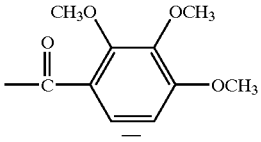 | H |
| No. 10 | C═O | $(CH_3)_2CH$— | H | H |
| No. 11 | C═O | $C_6H_5$— | H | H |
| No. 12 | C═O | 2-py | H | H |
| No. 13 | C═O | 3-py | 3-py-CO— | H |
| No. 14 | C═O | 4-py | H | H |
| No. 15 | C═O | 2-HOOC—$C_6H_4$— | H | H |
| No. 16 | C═O | trans-$HOOCCH_2CH$═CH— | H | H |
| No. 17 | CH | 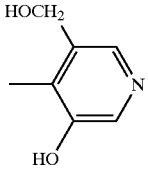 | H | — |
| No. 18 | CH | 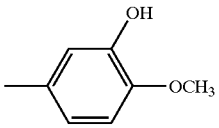 | H | — |
| No. 19 | CH | 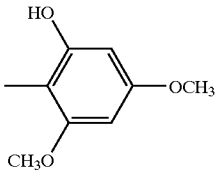 | H | — |

-continued
| No. | Y | R | R' | R" |
|---|---|---|---|---|
| No. 20 | CH | 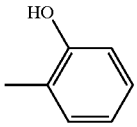 | H | — |
| No. 21 | CH | 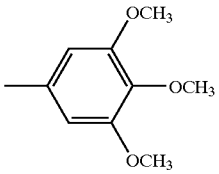 | H | — |
| No. 22 | CH | 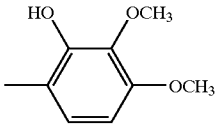 | H | — |
| No. 23 | CH | 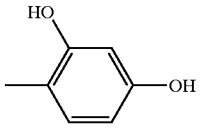 | H | — |
| No. 24 | CH | 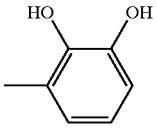 | H | — |
| No. 25 | CH | 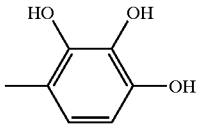 | H | — |
| No. 26 | CH | 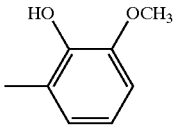 | H | — |
| No. 27 | CH | 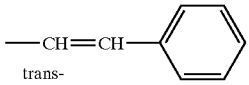 trans- | H | — |
| No. 28 | CH | 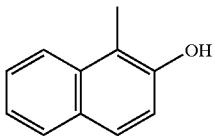 | H | — |
| No. 29 | CH | 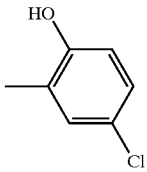 | H | — |

-continued
| No. | Y | R | R' | R" |
|---|---|---|---|---|
| No. 30 | CH | 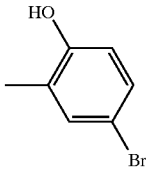 | H | — |
| No. 31 | CH | 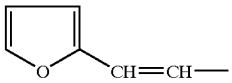 | H | — |
| No. 32 | CH | 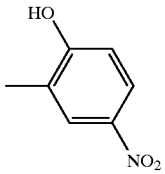 | H | — |
| No. 33 | CH | 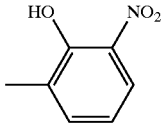 | H | — |
| No. 34 | CH | 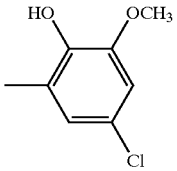 | H | — |
| No. 35 | CH | 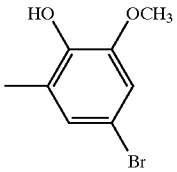 | H | — |
| No. 36 | CH | 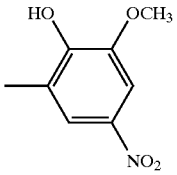 | H | — |
| No. 37 | CH | 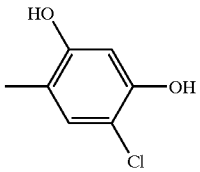 | H | — |
| No. 38 | CH | 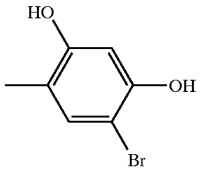 | H | — |

Pharmacological effect of huperzine A derivatives:

In the present invention a calorimetric method reported by Ellman was used to determine the effect of inhibition of the pharmaceutical on enzyme activity. The total volume of the solution of the enzyme activity reaction was 4 ml, which contained 0.3 mmol/L of acetylcholin iodide (acetylcholinesterase substrate), or 0.4 mmol/L of butyrylcholin iodide (butyrylcholinesterase substrate), 1 ml of the buffer solution of 25 mmol/L of phosphate of pH 7.4, and water to make up to 4 ml (including the amount of the enzyme solution and the testing reagent added afterwards). After the solution was kept at 37° C. for 5 minutes, 0.1–0.2 ml of enzyme solution (red cell membrane or serum of rat) was added, or 0.1–0.3 ml of the testing reagent was added at the same time. The solution was kept at the same temperature for another 8 minutes. Then 1 ml of 3% of sodium lauryl sulphate was added to terminate the reaction. Finally 1 ml of 0.2% 5,5-dithio-2,2'-nitro-benzoic acid solution was added for developing. "721" spectrophotometer was used to determine the density of light at 440 nm. A solution without addition of the pharmaceutical to inhibit the enzyme activity was used as a control (100%). A diagram was plotted with the percentage of the remaining enzyme activity against gram molecule concentration of the pharmaceutical, so as to obtain the dose of the pharmaceutical at 50% of inhibition of the enzyme activity, i.e., $IC_{50}$. The results of the test showed that all the derivatives exhibited inhibition effect on acetylcholinesterase; derivatives No. 1, No. 17, No. 18 and No. 19 exhibited remarkable inhibition effect on acetylcholinesterase; their effect was slightly weaker than that of huperzine A, but apparently stronger than that of physostigmine and galanthamine. They exhibited weaker inhibition effect on butyrylcholinesterase (pseudo enzyme) than huperzine A. Derivatives No. 1 and No. 17 exhibited greater selective inhibition effect on acetylcholinesterase than huperzine A (see Tables 1, 2 and 6). A study on kinetics of enzyme indicated that the combination of derivatives No. 17, No. 18 and No. 19 respectively with acetylcholinesterase was reversible.

The two memory model test, mouse passive escape operation (Platform jumping method) and 8-arm maze spatial distinction operation of rat, indicated that both derivatives No. 18 and No. 19 exhibited very strong effect, similar to that of the compound of formula (I), on improving memory (see Tables 3 and 4).

The critical toxicity test on mice indicated that LD50 of derivatives No. 18 and No. 19 were smaller than, only ⅓ of, that of the compound of formula (I) (see Table 5).

TABLE 1

In-vitro anticholinesterase effect of huperzine A derivatives (determined by colorimetric method)

| Compound No. | concentration for inhibition of 50% of enzyme activity ($IC_{50}$ μM) acetylcholinesterase (AChE) | butyrylcholinesterase (BuChE) | $IC_{50}$ ratio BuChE/AChE |
|---|---|---|---|
| 1 | 0.348 | 380.19 | 1092.5 |
| 2 | 9.05 | >346.7 | |
| 3 | 3.63 | >331.1 | |
| 4 | >12.88 | 58.9 | |
| 5 | >10.96 | >275.4 | |
| 6 | >12.3 | >309.1 | |
| 17 | 0.172 | 199.5 | 1159.9 |
| 18 | 0.151 | 107.2 | 709.9 |

TABLE 1-continued

In-vitro anticholinesterase effect of huperzine A derivatives (determined by colorimetric method)

| Compound No. | concentration for inhibition of 50% of enzyme activity ($IC_{50}$ μM) acetylcholinesterase (AChE) | butyrylcholinesterase (BuChE) | $IC_{50}$ ratio BuChE/AChE |
|---|---|---|---|
| 19 | 0.145 | 104.7 | 722.1 |
| 10 | >15.85 | 109.6 | |
| 11 | >14.45 | 363 | |
| compound(I) | 0.06309 | 63.09 | 1000 |
| Physostigmine | 0.251 | 1.259 | 5.02 |
| galanthamine | 1.995 | 12.59 | 6.3 |

AChE taken from rat's red cell membrane. BuChE taken from rat's serum.

TABLE 2

In-vitro anticholinesterase effect of huperzine A derivatives

| Compound No. | MW | concentration for inhibition of 50% of enzyme activity ($IC_{50}$ μM) acetylcholinesterase (AChE) | butyrylcholinesterase (BuChE) | $IC_{50}$ ratio BuChE/AChE |
|---|---|---|---|---|
| huperzine A | 242 | 0.0977 | 100.0 | 1023.3 |
| 1 | 342 | 0.3475 | 380.2 | 1094.1 |
| 12 | 376 | 0.1259 | 251.2 | 1995.2 |
| 15 | 390 | 0.6310 | 502.0 | 795.6 |
| 17 | 428 | 0.1718 | 199.5 | 1161.2 |
| 18 | 376 | 0.1514 | 107.2 | 708.2 |
| 19 | 406 | 0.1445 | 104.7 | 724.6 |
| 20 | 346 | 0.1778 | 125.9 | 708.1 |
| 21 | 420 | 0.1413 | 158.5 | 1121.3 |
| 22 | 406 | 0.1259 | 125.9 | 1000.0 |
| 23 | 362 | 0.2512 | 199.5 | 794.2 |
| 24 | 362 | 0.1000 | 158.5 | 1585.0 |
| 25 | 378 | 0.1585 | 251.2 | 1584.9 |
| 27 | 356 | 0.1259 | 100.0 | 794.3 |

MW: molecular weight

AChE taken from homogenate of rat's cortex. BuChE taken from rat's serum.

TABLE 3

Improvement by huperzine A derivatives on the condition of memory impairment caused by scopolamine in passive escape operation

| Group | dosage (mg/kg ip + po) | No. of mice | delitescence of get-down Δ (sec ± SEM) |
|---|---|---|---|
| physiological saline + physiological saline | −+− | 20 | 71.9 ± 12.9 |
| scopolamine + physiological saline | 2+ − | 20 | 29.5 ± 2.7 |
| scopolamine + derivative No. 18 | 2 + 0.2 | 20 | 67.7 ± 11.7** |
| | 3 + 0.3 | 20 | 64.0 ± 9.8* |
| | 2 + 0.4 | 20 | 48.7 ± 6.9 |
| physiological saline + physiological saline | −+− | 18 | 81.7 ± 19.0 |
| scopolamine + | 2+ − | 23 | 32.8 ± 8.2 |

TABLE 3-continued

Improvement by huperzine A derivatives on the condition of memory impairment caused by scopolamine in passive escape operation

| Group | dosage (mg/kg ip + po) | No. of mice | delitescence of get-down Δ (sec ± SEM) |
|---|---|---|---|
| physiological saline | | | |
| scopolamine + | 2 + 0.1 | 11 | 48.9 ± 12.6 |
| derivative No. 19 | 2 + 0.2 | 16 | 71.6 ± 14.5 |
| | 2 + 0.3 | 21 | 99.8 ± 16.4** |
| | 2 + 0.4 | 18 | 92.2 ± 15.5* |

Δ: Once trained, the mice were administered, and tested after 24 hours. comparison with the physiological saline group P < 0.01
**comparison with scopolamine group *P < 0.05, **P < 0.01

TABLE 4

Improvement by huperzine derivatives on the condition of memory impairment caused by scopolamine in spatial distinction operation

| Group | dosage (mg/kg ip + po) | No. of rats | No. of mistakes in operation before reaching the standard Δ X + SEM) refer-ence memory | working memory |
|---|---|---|---|---|
| physiological saline + physiological saline | −+− | 24 | 0.42 ± 0.1 | 0.08 ± 0.01 |
| scopolamine + physiological saline | 0.2+ − | 6 | 1.67 ± 0.21 | 0.33 ± 0.42 |
| scopolamine + derivative No. 19 | 0.2 ± 0.1 | 6 | 1.33 ± 0.21 | 1.33 ± 0.49** |
| | 0.2 ± 0.3 | 6 | 0.33 ± 0.21** | 0.17 ± 0.17** |
| physiological saline + physiological saline | −+− | 24 | 0.33 ± 0.13 | 0.08 ± 0.006 |
| scopolamine + physiological saline | 0.125+ − | 6 | 2.0 ± 0.45 | 2.0 ± 0.52 |
| scopolamine + derivative No. 18 | 0.124 + 0.2 | 6 | 0.67 ± 0.33** | 0.33 ± 0.13** |
| physiological saline + physiological saline | −+− | 14 | 0.21 ± 0.11 | 0.07 ± 0.07 |
| scopolamine + physiological saline | 0.15+ − | 7 | 2.14 ± 0.14 | 2.57 ± 0.29 |
| scopolamine + huperzine A | 0.15 + 0.25 | 10 | 0.57 ± 0.30** | 0.86 ± 0.14** |

Δ: 8-arm maze test. After trained to reach the standard (no. of mistake less than one per day for three successive days), the rats were tested. The rat first entering the arm on which there is no food is taken as the reference emory mistake. The rat re-entering the arm on which there is food is taken as the working memory mistake, comparison with the physiological saline group P > 0.01
**comparison with scopolamine group P < 0.01

TABLE 5

Critical toxicity of huperzine A derivatives on mice (Bliss method)

| Compound | mg/kg p.o. (95% confidence limit)* $LD_{50}$ | $LD_{50}$ |
|---|---|---|
| compound (I) | 3.1(3.5–3.8) | 4.6(4.2–5.1) |
| derivative No. 18 | 9.6(7.3–12.5) | 14.4(12.9–16.4) |
| derivative No. 19 | 11.1(9.6–12.9) | 14.1(15.5–20.5) |

*10 mice per group, with equal no. of males and females.

Test of each pharmaceutical was carried out using 4–5 dosage group.

Mortality within 7 days was observed.

TABLE 6

In-vitro anticholinesterase effect of huperzine A derivatives

| Compound | inhibition activity AChE | | BuChE | |
|---|---|---|---|---|
| No. | 1(μM) | $IC_{50(M)}$ | 10(μM) | BuChE/AChE |
| (18) | 90.2 | $8.4 \times 10^{-8}$ | 0 | >500 |
| (20) | 83.7 | $9.4 \times 10^{-8}$ | 0 | >500 |
| (21) | 84.9 | $1.0 \times 10^{7}$ | 0 | >500 |
| (22) | 68.7 | | 0 | |
| (23) | 34.4 | | 0 | |
| (15) | 60.8 | | 0 | |
| (24) | 78.3 | $2.8 \times 10^{-7}$ | 0 | >100 |
| (25) | 62.0 | | 0 | |
| (27) | 84.0 | $1.1 \times 10^{-7}$ | 3.3 | >500 |
| (26) | 79.7 | $1.8 \times 10^{-7}$ | 1.1 | >300 |
| (16) | 80.7 | $2.1 \times 10^{-7}$ | 1.8 | >200 |
| (14) | 76.4 | $3.6 \times 10^{-7}$ | 2.5 | >100 |
| (44) | 85.6 | $1.1 \times 10^{-7}$ | 1.8 | >500 |
| (45) | 87.0 | $1.0 \times 10^{-7}$ | 1.8 | >500 |
| (46) | 78.7 | $2.9 \times 10^{-7}$ | 1.2 | >100 |
| E-2020 | 86.2 | $6.6 \times 10^{-8}$ | 2.9 | >500 |
| huperzine A | 88.3 | $1.2 \times 10^{-7}$ | 0 | >500 |

The results of the above pharmacological study show that derivatives No. 17, No. 18 and No. 19 are highly effective selective inhibitors of acetylcholinesterase and have lower critical toxicity than compound (I). Hence, it can be deduced that they have prospect of clinical application and development for use in the treatment of relieving serious amyasthenia and of dysmnesia caused by failure in central cholinergic system.

EXAMPLE 1

Preparation of Derivative No. 2

Compound (I) (0.50 mmole) into 5 ml three-neck flask was weight out. 20 ml of anhydrous pyridine was added to dissolve compound (I). While cooling in ice-bath, phenyl acetyl chloride (0.55 mmole) was added dropwise. Then the whole mixture was stirred overnight at room temperature (25° C.). When thin-layer chromatography indicated substantial disappearance of the starting materials, the reaction was stopped. Pressure was reduced by means of water pump to vaporize pyridine. Separation was carried out using silica gel layer chromatography. Elution was carried out with dichloromethane:acetone:methanol=5:45:5 to produce the crude product, which was recrystallized using a mixed solvent of acetone and petroleum ether to produce the product with 75% yield.

UV $\lambda_{max}$=229 nm (∈=17360); $\lambda_{max}$=316 nm(∈=9320); $[\alpha]^{p25°\ C.}$=29.43; $^1$HNMR: [$CDCl_3$]; 3H 6.31(1H,d,J=9.9 Hz); 4H 7.20 (1H,d,J=9.9 Hz); 10H 2.89(2H,m); 9H 3.52 (1H,m); 8H 5.38(1H,d,J=5.0 Hz); 14-H 1.62(3H,d,J=6.7 Hz); 13-H 5.08(1H,q,J=6.7 Hz); 6-H 2.15,2.45(2H,m); 12-H 1.50(3H,s); 2',4'-H 7.36(2H,m); 3',5'-H 7.29(2H,m); 6'-H 7.24(1H,m); 7'-H 3.59(s); MS(m/z) 360($M^+$) 345 269 252 227 224 210(100%) 91; mp: 171–173° C.; IR: $\upsilon^{max}$ 3280, 1660(s), 1620(s), 1550, 1450, 1350, 1300, 1175, 1130, 840, 620 $cm^{-1}$ The same process was used to prepare derivatives No. 3, No. 5, No. 6, No. 7, No. 8, No. 9, No. 10, No. 11, and No. 13.

EXAMPLE 2

Preparation of Derivative No. 4

Compound (I) (0.5 mmole) into 50 ml three-neck flask was weight out. 20 ml of anhydrous pyricline to dissolve compound (I) was added. While cooling in ice-bath, DBU (0.6 mmole) was first added, and then 0.55 mmole of hydrochloric acid pyridine-2-formyl chloride was added. The whole mixture was placed overnight at room temperature. When thin-layer chromatography determination indicated substantial completion of the reaction, pressure was reduced by means of water pump to vaporize pyridine. Separation was carried out using silica gel layer chromatography. Elutioni was carried out with dichloromethane:acetone:methanol=50:45:5 to produce the crude product, which was recrystallized using a mixed solvent of acetone and petroleum ether to produce the product with 74% yield.

UV $\lambda_{max}$=226 nm ($\in$=1.35×10$^4$); $\lambda_{max}$=264 nm ($\in$=5.4·10$^3$); $\lambda_{max}$=315 nm ($\in$=5730); $[\alpha]_D$=77.85°; $^1$HNMR: [$CDCl_3$]; 3-H 6.36(1H,J=9.2 Hz); 4-H 7.44(1H,J=9.2 Hz); 10-H 3.05(2H,m); 9-H 3.74(1H,m); 8-H 5.42(1H,d,J=4.7 Hz); 14-H 1.65(3H,d,J=6.6 Hz); 13-H 5.35(1H,q=6.6 Hz); 6-H 2.42(2H,s); 12-H 1.55(3H,s); 2'-H 8.58(1H,m); 4'-H 7.85(1H,m); 5'-H 7.48(1H,m); 6'-H' 8.15(1H,m); MS(m/z) 347($M^+$), 241(100%) 169, 149, 106, 95, 79, 71, 55; mp: 170–171° C.; IR: $u_{max}$ 3450, 2900, 1660(s), 1615(s), 1530(s), 1460, 1300, 1180, 1140, 1000, 830, 750 cm$^{-1}$ The same process was used to prepare derivatives No. 12 and No. 14.

EXAMPLE 3

Preparation of Derivative No. 19

Compound (I) (0.5 mmole) was weight out into 50 ml three-neck flask. Anhydrous ethanol and 4,6-dimethoxy-2-hydroxy benzaldehyde (0.51 mmole) were added. The mixture was heated slightly under reflux. Through a water segregator part of the ethanol was vaporized continuously. The solvent in the reaction was constantly replenished. The reaction was carried out for several hours and the reaction state was constantly determined by means of thin-layer chromatography. When the reaction was completed, the pressure was reduced to remove the ethanol to produce a solid crude product, which was recrystallized using a mixed solvent of acetone and petroleum ether to produce the product with 92% yield.

The same process was used to prepare derivatives No. 17, 18, 20, 21, 22, 23, 24, 25, 26, 27, 28, 29, 30, 31, 32, 33, 34, 35, 36, 37, 38, 39, 40, 41, 42, and 43.

Derivative No. 19 m.p. 207–210° C.; MS: m/z 406($M^+$); 391($M^+$-$CH_3$), 351($M^+$-$C_4H_7$); $^1$H NMR ($CDCl_3$); 1-H 13.12(1H,br,s); 3-H 6.41(1H,d,J=9.1 Hz); 4-H 7.25(1H,d,J=9.1 Hz); 6-H 2.85 (2H,s); 8-H 3.45(1H,d,J=4.7 Hz); 9-H 3.61(1H,m); 10-H 2.85(2H,m); 12-$H_3$ 1.60(3H,s); 13-H 5.22(1H,q,J=7.7 Hz); 14-$H_3$ 1.25(3H,d,J=7.7 Hz); 2'-OH 14.58(1H,br,s); 3'-H 5.57 (1H,s); 4'-$OCH_3$ 3.79(3H,s); 5'-H 5.85(1H,s); 6'-$OCH_3$ 3.70 (3H,s); 7'-H 8.15(1H,s); IR: $\upsilon_{max}$ 3480(m), 2960(s), 2930(s), 2870(s), 1670(s), 1620(s), 1540(s), 1450(s), 1330 (s), 1300 (s), 1218(sh), 1186(m), 1155(s), 1110(s), 1080(m), 1050(m), 1000(m), 930(m), 840(s), 730(m), 670(m), 610(m), 520(s) cm$^{-1}$.

Derivative No. 20

$^1$H NMR ($CDCl_3$): 1-H 12.72(1H,br,s); 3-H 6.34(1H,d, J=9.4 Hz); 4-H 7.11(1H,d,J=9.4 Hz); $6_a$-H 2.79(1H,d,J=16.0 Hz); $6_b$-H 2.75(1H,d,J=16.0 Hz); 8-H 5.41(1H,d,J=5.0 Hz); 9-H 3.63(1H,m); $10_a$-H 2.95(1H,dd,J=16.6, 4.9 Hz); $10_b$-H 2.27(1H,d,J=16.6 Hz); 12-H 1.57(3H,s); 13-H 5.07(1H,q,J=6.8 Hz); 14-H 1.55(3H,d,J=6.8 Hz); 2'-OH 13.77(1H,br,s); 3'-H 6.94(1H,d,J=8.4 Hz); 4'-H 7.30(1H,t with small splitts, J=8.4 Hz); 5'-H 6.85(1H,t with small splitts, J=7.4 Hz); 6'-H 7.22(1H,dd,J=7.4, 1.6 Hz); 7'-H 8.31(1H,s); MS: 346($M^+$), 331, 317, 303, 291, 253, 239, 226, 210, 197, 184, 167, 128, 121, 97. IR: $\upsilon_{max}$ 3420, 2900, 1660, 1620, 1580, 1560, 1500, 1460, 1420, 1380, 1350, 1280, 1205, 1150, 1120, 1080, 1010, 970, 910, 840, 790, 755(s), 650, 630, 610, 520 cm$^{-1}$ Derivative No. 21;

$^1$H NMR ($CDCl_3$); 1-H 12.87(1H,br,s); 3-H 6.32(1H,d, J=9.4 Hz); 4-H 7.07(1H,d,J=9.4 Hz); $6_a$-H 2.79(1H,d,J=16.0 Hz); $6_b$-H 2.75(1H,d,J=16.0 Hz); 8-H 5.43(1H,d,J=5.0 Hz); 9-H 3.63(1H,m); $10_a$-H 2.97(1H,dd,J=16.0, 4.0 Hz); $10_b$-H 2.18(1H,d,J=16.0 Hz); 12-H 1.58(3H,s); 13-H 5.14(1H,q,J=6.8 Hz); 14-H 1.57(3H,d,J=6.8 Hz); 2',6'-2H 7.04(2H,s); 7'-H 8.25(1H,s); 3',5'-2($OCH_3$) 3.87(6H,s); 4'-$OCH_3$ 3.84 (3H,s); MS: 420($M^+$), 405($M^+$-$CH_3$), 391, 365, 351, 313, 284, 239, 226, 210, 196, 181, 140, 124. IR: $\upsilon_{max}$ 2940, 1660(s), 1590, 1560, 1500, 1565, 1420, 1370, 1330, 1300, 1230, 1190, 1130(s), 1005, 960, 930, 840, 770, 735, 725, 660, 605, 540, 530 cm$^{-1}$.

Derivative No. 22

$^1$H NMR($CDCl_3$): 1-H 13.03(1H,br,s); 3-H 6.34(1H,d,J=9.4 Hz); 4-H 7.14(1H,d,J=9.4 Hz); 6-$H_2$ 2.73(2H,s); 8-H 5.39(1H,d,J=4.7 Hz); 9-H 3.61(1H,m); $10_a$-H 2.94(1H,dd, J=16.8, 4.9 Hz); $10_b$-H 2.27(1H,d,J=16.8 Hz); 12-H 1.55 (3H,s); 13-H 5.09(1H,q,J=6.8 Hz); 14-H 1.54(3H,d,J=6.8 Hz); 2'-OH 14.39(1H,br.s); 3'-$OCH_3$ 3.87(3H,s); 4'-$OCH_3$ 3.85(3H,s); 5'-H 6.43(1H,d,J=8.7 Hz); 6'-H 6.91(1H,d,J=8.7 Hz); 7'-H 8.14(1H,s); MS: 406($M^+$), 391($M^+$-$CH_3$), 373, 351, 239, 226, 197, 182, 167, 139, 101; IR: $\upsilon^{max}$ 3450–3350 (br), 2940(m), 1660(s), 1620(s), 1555, 1510, 1455, 1415, 1290, 1270(s), 1210, 1110(s), 1060, 970, 930, 835, 785, 695, 675, 640, 625 cm$^{-1}$.

Derivative No. 23

$^1$H NMR($d_6$-DMSO): 1-H 11.48(1H,br,s); 3-H 6.13(1H, d,J=9.4 Hz); 4-H 7.07(1H,d,J=9.4 Hz); $6_a$-H 2.68(1H,d,J=16.7 Hz); $6_b$-H 2.59(1H,d,J=16.7 Hz); 8-H 5.48(1H,d,J=4.7 Hz); 9-H 3.65(1H,m); $10_a$-H 2.77(1H,dd,J=16.3, 4.0 Hz); $10_b$-H 2.28(1H,d,J=16.3 Hz); 12-H 1.59(3H,s); 13-H 5.05 (1H,q,J=6.8 Hz); 14-H 1.60(3H,d,J=6.8 Hz); 2'-OH 14.40 (1H,br,s); 3'-H 6.18(1H,s); 4'-OH 10.09(1H,br,s); 5'-H 6.30 (1H,d, with small splitts, J=8.4 Hz); 6'-H 7.31(1H,d,J=8.4 Hz); 7'-H 8.47(1H,s); MS: 362($M^+$), 347, 319, 307, 242, 226, 210, 197, 167, 137. IR: $\upsilon_{max}$ 3500–2800(br), 1665(s), 1625(s), 1605(s), 1550, 1540, 1450, 1345, 1300, 1230, 1180, 1120, 1080, 975 cm$^{-1}$.

Derivative No. 24

$^1$H-NMR($CDCl_3$): 1-H 13.09(1H,br,s); 3-H 6.37(1H,d,J=9.4 Hz); 4-H 7.15(1H,d,J=9.4 Hz); 6-$H_2$ 2.76(2H,s); 8-H 5.42(1H,d,J=5.0 Hz); 9-H 3.60(1H,m); $10_a$-H 2.96(1H,dd, J=16.5, 4.9 Hz); $10_b$-H 2.32(1H,d,J=16.5 Hz); 12-H 1.56 (3H,s); 13-H 5.11(1H,q,J=6.8 Hz); 14-H 1.58(3H,d,J=6.8 Hz); 2'-OH 13.09(1H,br,s); 3'-OH 9.83(1H,br,s); 4'-H 6.68 (1H,dd,J=8.1, 1.5 Hz); 5'-H 6.57(1H,t,J=7.8 Hz); 6'-H 6.91 (1H,dd,J=7.6, 1.5 Hz); 7'-H 8.08(1H,s); MS: 362($M^+$), 347 ($M^+$-$CH_3$), 307, 253, 239, 226 197, 167, 149, 138, 137, 109, 92, 81. IR: $\upsilon_{max}$ 3500–2800(br), 1660(s), 1625(s), 1545, 1460, 1370, 1275, 1240, 1120, 1080, 1060, 1020, 835, 775, 740(s), 640, 630, 525 cm$^{-1}$.

Derivative No. 26

$^1$HNMR($CDCl_3$): 1-H 13.10(1H,br,s); 3-H 6.33(1H,d J=9.4 Hz); 4-H 7.12(1H,d,J=9.4 Hz); 6-$H_2$ 2.75(2H,s); 8-H 5.41(1H,d,J=4.8 Hz); 9-H 3.62(1H,m); $10_a$-H 2.95(1H,dd,

J=16.5, 4.9 Hz); $10_b$-H 2.27(1H,d,J=16.5 Hz); 12-$H_3$ 1.57 (3H,s); 13-H 5.08(1H,q,J=6.8 Hz); 14-H 1.54(3H,d,J=6.8 Hz); 2'-OH 14.36(1H,br,s); 3'-$OCH_3$ 3.86(3H,s); 4'-H 6.83 (1H,dd,J=7.9, 1.5 Hz); 5'-H 6.76 (1H,t,J=7.9 Hz); 6'-H 6.89(1H,dd,J=7.9, 1.5 Hz); 7'-H 8.27(1H,s); MS: 376($M^+$), 361, 346, 331, 306, 270, 253, 239, 226, 210, 197, 167, 152, 109, 106, 82. IR: $\upsilon^{max}$ 3450–3360, 2940–2980, 1660(s), 1620(s), 1555, 1465(s), 1255(s), 1190, 1170, 1115, 1085, 970, 930, 840, 780, 740, 680, 640, 630, 520 $cm^{-1}$.

Derivative No. 27

$^1$HNMR($CDCl_3$): 1-H 12.80(1H,br,s); 3-H 6.34(1H,d,J=9.4 Hz); 4-H 7.07(1H,d,J=9.4 Hz); 6-$H_2$ 2.72(2H,s); 8-H 5.40(1H,d,J=5.0 Hz); 9-H 3.61(1H,m); $10_a$-H 2.94(1H,dd, J=16.2, 3.6 Hz); $10_b$-H 2.17(1H,d,J=16.2 Hz); 12-H 1.56 (3H,s); 13-H 5.08(1H,q,J=6.8 Hz); 14-H 1.57(3H,d,J=6.8 Hz); 2',6'-2H 7.45(2H,dd,J=6.8, 1.4 Hz); 3',5',8'-3H 7.30 (3H,m); 4'-H 7.06(1H,m); 7'-H 6.99 (1H,d,J=15.9 Hz); 9'-H 8.06(1H,d,J=8.1 Hz); MS: 356($M^+$), 341($M^+$-$CH_3$), 327, 301, 265, 237, 226, 210, 197, 167, 131, 115, 91, 77. IR: $\upsilon_{max}$ 3600–3400(br), 2950–2850(br), 1660(s), 1632, 1620, 1550, 1465, 1445, 1300(m), 1175, 1115, 975, 825, 750(s), 690(s), 630, 620, 520 $cm^{-1}$.

Derivative No. 28

$^1$HNMR($CDCl_3$): 1-H 12.76(1H,br,s); 3-H 6.38(1H,d,J=9.3 Hz); 4-H 7.12(1H,d,J=9.3 Hz); $6_a$-H 2.81(1H,d,J=16.0 Hz); $6_b$-H 2.78(1H,d,J=16.0 Hz); 8-H 5.46(1H,br,s); 9-H 3.67(1H,m); $10_a$-H 3.00(1H,dd,J=16.4, 4.5 Hz); $10_b$-H 2.31 (1H,d,J=16.4 Hz); 12-H 1.62(3H,s); 13-H 5.07(1H,q,J=6.6 Hz); 14-H 1.60(3H,d,J=6.6 Hz); 2'-OH 13.76(1H,br,s); 3'-H 6.94(1H,d,J=8.7 Hz); 4'-H 7.29(1H,dd,J=8.7, 2.3 Hz); 5',6', 7',8'-4H 7.25(4H,m); 11'-H 8.30(1H,s); MS(m/z): 396($M^+$, 3%), 381($M^+$-$CH_{3,1}$), 226(2), 172(4), 144(2), 127(1), 115 (5), 85(13), 71(22), 57(100). IR(KBr): 3408, 1660, 1626, 1479, 1280 $cm^{-1}$.

Derivative No. 30

$^1$HNMR($CDCl_3$): 1-H 10.92(1H,br,s); 3-H 6.42(1H,d,J=9.3 Hz); 4-H 7.15(1H,d,J=9.3 Hz); $6_a$-H 2.82(1H,d,J=17.2 Hz); $6_b$-H 2.76(1H,d,J=17.2 Hz); 8-H 5.47(1H,br,s); 9-H 3.69(1H,m); $10_a$-H 2.99(1H,dd,J=16.0, 3.7 Hz); $10_b$-H 2.30 (1H,d,J=16.0 Hz); 12-H 1.63(3H,s); 13-H 5.07(1H,q,J=6.8 Hz); 14-H 1.61(3H,d,J=6.8 Hz); 3'-H 6.89(1H,d,J=6.8 Hz); 4',6'-2H 7.42(2H,m); 7'-H 8.30(1H,s); MS(m/z): 426($M^+$+2,43%), 424($M^+$, 43), 411[($M^+$+2)-$CH_3$,42], 409($M^+$-$CH_3$, 45), 369(11), 289(5), 253(18), 239(33), 226(100), 210(54), 197(47), 167(31), 128(31), 115(46), 91(32), 77(59), 57(81). IR(KBr): 3400, 1660, 1630, 1475, 1280, 823 $cm^{-1}$.

Derivative No. 32

$^1$HNMR($CDCl_3$): 1-H 12.70(1H,br,s); 3-H 6.39(1H,d,J=9.4 Hz); 4-H 7.11(1H,d,J=9.4 Hz); $6_a$-H 2.81(1H,d,J=16.2 Hz); $6_b$-H 2.77(1H,d,J=16.2 Hz); 8-H 5.45(1H,br,s); 9-H 3.67(1H,m); $10_a$-H 2.99(1H,dd,J=16.7, 4.9 Hz); $10_b$-H 2.31 (1H,d,J=16.7 Hz); 12-H 1.62(3H,s); 13-H 5.06(1H,q,J=6.8 Hz); 14-H 1.60(3H,d,J=6.8 Hz); 2'-OH 13.80(1H,br,s); 3'-H 6.89(1H,d,J=8.7 Hz); 4'-H 7.42(1H,dd,J=8.7, 2.4 Hz); 6'-H 7.39(1H,d,J=2.4 Hz); 7'-H 8.29(1H,s); MS(m/z): 392($M^+$+1,11%), 391($M^+$,45), 376($M^+$-$CH_3$,60), 242(18), 226(53), 101(28), 83(53), 59(100). IR(KBr): 3419, 1660, 1616, 1549, 1336, 833 $cm^{-1}$.

Derivative No. 33

$^1$HNMR($CDCl_3$): 1-H 12.40(1H,br,s); 3-H 6.42(1H,d,J=9.5 Hz); 4-H 7.15(1H,d,J=9.5 Hz); $6_a$-H 2.84(1H,d,J=16.3 Hz); $6_b$-H 2.77(1H,d,J=16.3 Hz); 8-H 5.47(1H,br,s); 9-H 3.70(1H,m); $10_a$-H 3.00(1H,dd,J=16.0, 4.9 Hz); $10_b$-H 2.39 (1H,d,J=16.0 Hz); 12-H 1.58(3H,s); 13-H 5.12(1H,q,J=6.8 Hz); 14-H 1.63(3H,d,J=6.8 Hz); 2'-OH 15.59(1H,br,s); 4'-H 8.16(1H,d,J=7.8 Hz); 5'-H 6.77(1H,t,J=7.8 Hz); 6'-H 7.46 (1H,d,J=7.8 Hz); 7'-H 8.24(1H,s); MS(m/z): 391($M^+$,66%), 376($M^+$-$CH_3$,41), 356(45), 328(18), 288(14), 239(15), 226 (100), 210(25), 197(22), 83(61). IR(KBr): 3431, 1662, 1633, 1529, 1352, 1242, 754 $cm^{-1}$.

Derivative No. 34

$^1$HNMR($CDCl_3$): 1-H 12.87(1H,br,s); 3-H 6.38(1H,d,J=9.6 Hz); 4-H 7.13(1H,d,J=9.6 Hz); 6-$H_2$ 2.78(2H,s); 8-H 5.46(1H,br,s); 9-H 3.67(1H,m); $10_a$-H 3.00(1H,dd,J=16.5, 4.9 Hz); $10_b$-H 2.32(1H,d,J=16.5 Hz); 12-H 1.62(3H,s); 13-H 5.09(1H,q,J=6.7 Hz); 14-H 1.59(3H,d,J=6.7 Hz); 2'-OH 14.42(1H,br,s); 3'-$OCH_3$ 3.90(3H,s); 4',6'-2H 6.86 (2H,m); 7'-H 8.22(1H,s); MS(m/z): 412($M^+$+2,0.3%), 410 ($M^+$,1.2), 395($M^+$-$CH_3$,0.5), 239(1.4), 216(2), 83(100). IR(KBr): 3421, 2933, 1660, 1618, 1471, 1253, 839 $cm^{-1}$.

Derivative No. 35

$^1$HNMR($CDCl_3$): 1-H 12.80(1H,br,s); 3-H 6.38(1H,d,J=9.3 Hz); 4-H 7.13(1H,d,J=9.3 Hz); 6-$H_2$ 2.78(2H,s); 8-H 5.46(1H,br,s); 9-H 3.67(1H,m); $10_a$-H 3.00(1H,dd,J=16.7, 5.1 Hz); $10_b$-H 2.32(1H,d,J=16.7 Hz); 12-H 1.62(3H,s); 13-H 5.08(1H,q,J=6.8 Hz); 14-H 1.59(3H,d,J=6.8 Hz); 2'-OH 14.45(1H,br,s); 3'-$OCH_3$ 3.89(3H,s); 4',6'-2H 7.00 (2H,m); 7'-H 8.21(1H,s); MS(m/z): 456($M^+$2,79), 454($M^+$, 7a), 441[($M^+$+2)-$CH_3$, 40], 439($M^+$-$CH_3$,42), 401(7), 399 (8), 285(14), 239(24), 226(100), 210(33), 197(37), 83(84). IR(KBr): 3431, 1660, 1624, 1471, 1252 $cm^{-1}$.

EXAMPLE 4

Preparation of Derivative No. 15

Compound (I) (0.5 mmole) was weight out into 50 $\mu$l three-neck flask. 20 ml of anhydrous pyridine was added to dissolve compound (I). While cooling in ice-bath, o-phthalic acid anhydride was added. The mixture was stirred overnight at room temperature. When thin-layer chromatography determination indicated substantial completion of the reaction, the pressure was reduced by means of water pump to vaporize pyridine. Separation was carried out using silica gel layer chromatography. The development agent dichloromethane:methanol=3:1 was used to produce the crude product, which was recrystallized using propanol to produce white powders of derivative No. 15 with 78% yield.

The same process was used to prepare derivatives No. 1 to No. 16.

$^1$H NMR($d_6$-DMSO): 3-H 6.09(1H,d,J=9.4 Hz); 6-$H_2$ 2.51(2H,s); 8-H 5.44(1H,d,J=4.8 Hz); 9-H 3.56(1H,m); $10_a$-H 2.66(1H,dd,J=16.8, 4.6 Hz); $10_b$-H 2.09(1H,d,J=16.8 Hz); 12-$H_3$ 1.51(3H,s); 13-H 5.60(1H,q,J=6.8 Hz); 14-$H_3$ 1.62(3H,d,J=6.8 Hz); 3',4',5' and 4-H 7.51(4H,m); 6'-H 7.73(1H,d,J=7.5 Hz); N-H(amide) 7.90(1H,br,s); COO-H 8.46(1H,br,s); IR: $\upsilon_{max}$ 3650–2400, 1710, 1655, 1605, 1546, 1450, 1300 $cm^{-1}$ MS m/z: 372($M^+$), 357, 343, 329, 242, 227, 187, 147, 104(100).

EXAMPLE 5

Preparation of Derivative No. 44

Under argon gas stream 150 mg (0.620 mmole) of huperzine A and 200 mg of 4A molecular sieve were suspended in 4 ml of benzene. 76 $\mu$l (0.86 mmol) of pyridine-3-acetaldehyde and 20 mg of p-toluene sulphonic acid monohydrate were added. After reflux for three hours, the mixture was allowed to cool, and then neutralized with triethyl amine. The reaction solution was filtered with celite. After concentration, the residue was refined through silica gel column chromatography (methanol:dichloromethane=1:20) to produce derivative No. 44, a colorless solid (183 mg, 89% yield).

The same process was used to prepare derivatives No. 45 and No. 46, with 84% and 82% yield respectively.

Derivative No. 44

NMR($CDCL_3$) 1.64(3H,d,J=7.0 Hz), 1.65(3H,s); 2.25 (1H,d,J=16.0 Hz), 2.82(1H,d,J=17.0 Hz); 2.86(1H,d,J=16.0 Hz), 3.07(1H,dd,J=5.0,17.0 Hz) 8.65–3.75(1H,m); 5.14(1H, q,J=7.0 Hz), 5.50(1H,d,J=5.0 Hz); 6.34(1H,d,J=8.5 Hz), 7.09(1H,d,J=9.5 Hz); 7.40(1H,dd,J=5.0,8.0 Hz), 8.28(1H,dt, J=2.0,8.0 Hz), 8.47(1H,s); 8.70–8.72(1H,m), 8.94–8.96(1H, m), MS: 331($M^+$), 316(base), 226; HRMS calculated value: molecular formula $C_{22}H_{21}N_2O(M^+)$: 331.16846; experimental value: 331.16888

Derivative No. 45

NMR($CDCL_3$) 1.64(3H,d,J=7.0 Hz), 1.65(3H,s); 2.25 (1H,d,J=16.0 Hz), 2.82(1H,d,J=16.5 Hz); 2.86(1H,d,J=16.0 Hz), 3.07(1H,dd,J=5.0,16.5 Hz),3.61–3.70(1H,m); 5.10(1H, q,J=7.0 Hz), 5.50(1H,d,J=4.0 Hz); 6.39(1H,d,J=9.5 Hz), 7.05(1H,d,J=9.5 Hz); 7.11–7.73(2H,m), 8.41(1H,s), 8.73–8.79(2H,m), MS: 331($M^+$), 316(base), 226; HRMS calculated value: molecular formula $C_{22}H_{21}N_3O(M^+)$: 331.16846; experimental value: 331.18836

Derivative No. 46

NMR($CDCL_3$) 1.64(3H,d,J=6.5 Hz), 1.65(3H,s); 2.24 (1H,d,J=16.0 Hz), 2.82(1H,d,J=16.5 Hz); 2.85(1H,d,J=16.0 Hz), 3.07(1H,dd,J=5.0,16.5 Hz),3.67–3.70(1H,m); 3.96(6H, s), 5.22(1H,q,J=6.5 Hz), 5.30(1H,s); 5.47–5.49(1H,m), 6.39 (1H,d,J=9.5 Hz), 7.12(1H,s), 7.15(1H,d,J=9.5 Hz), 8.29(1H, s); MS: 406($M^-$,base), 391, 228, 167 HRMS calculated value: molecular formula $C_{24}H_{26}N_2O_4(M^+)$: 406.18926; experimental value: 406.18949

We claim:

[1. A huperzine A compound having tile following structural formula (II)

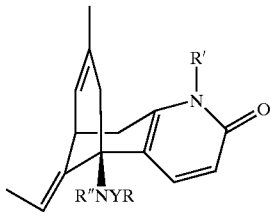

wherein Y and —R" together form═CH, R is

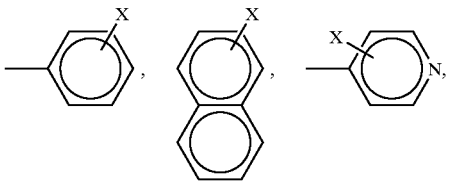

X is hydrogen, $C_1$–$C_5$ lower alkyloxy, nitro, halogen, hydroxymethyl, hydroxy, amino substituted by two $C_1$–$C_5$ lower alkyls or —CH═CH—G group, is phenyl or furanyl and R' is hydrogen.]

2. A method of treating [myasthenia] *amyasthenia* by inhibiting cholinesterase comprising administering a huperzine A compound according to claim [1] *10* to a patient in need of such treatment in an amount effective to inhibit cholinesterase.

3. A method of treating dysmnesia, caused by a failure in central cholinergic system by inhibiting cholinesterase comprising administering a huperzine A compound according to claim [1] *10* to a patient in need of such treatment in an amount effective to inhibit cholinesterase.

4. A method of inhibiting cholinesterase comprising administering a huperzine A compound according to claim [1] *10* in an amount effective to inhibit cholinesterase to a patient in need of such treatment.

5. A method of inhibiting cholinesterase according to claim 4, wherein said cholinesterase is an acetylcholinesterase.

6. A method of inhibiting cholinesterase according to claim 4, wherein the cholinesterase is butyrylcholinesterase.

7. A method of improving memory impairment comprising administering a huperzine A compound according to claim [1] *10* in an amount effective to improve [mnemory imnpairmient] *memory impairment* to a patient in need of such treatment.

8. A compound according to claim [1] *10*, wherein R" and Y are ═CH, prepared by a process of condensing huperzine A and the corresponding substituted aldehyde in an anhydrous solvent.

9. A method of inhibiting cholinesterase according to claim 4, wherein said huperzine A compound exhibits weaker inhibition effect on butyrylcholinesterase than huperzine A.

*10. A huperzine A compound of the formula*

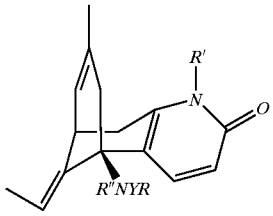

*wherein*

*Y and —R" together form a ═CH group;*

*R is*

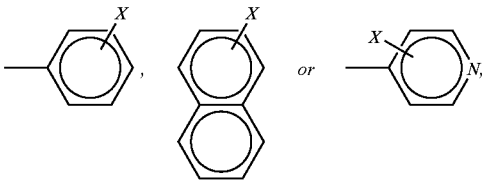

*wherein X is selected from the group consisting of hydrogen, $C_1$–$C_5$ lower alkoxy, nitro, halogen, hydroxymethyl, hydroxy, amino substituted by two $C_1$–$C_5$ lower alkyls and —CH═CH—G,*

*wherein G is phenyl or furanyl; and*

*R' is hydrogen.*

*11. A huperzine A compound of the formula*

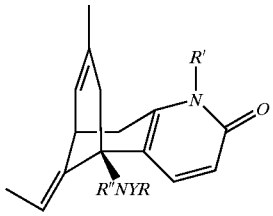

wherein

Y and —R" together form =CH;

R is selected from the group consisting of:

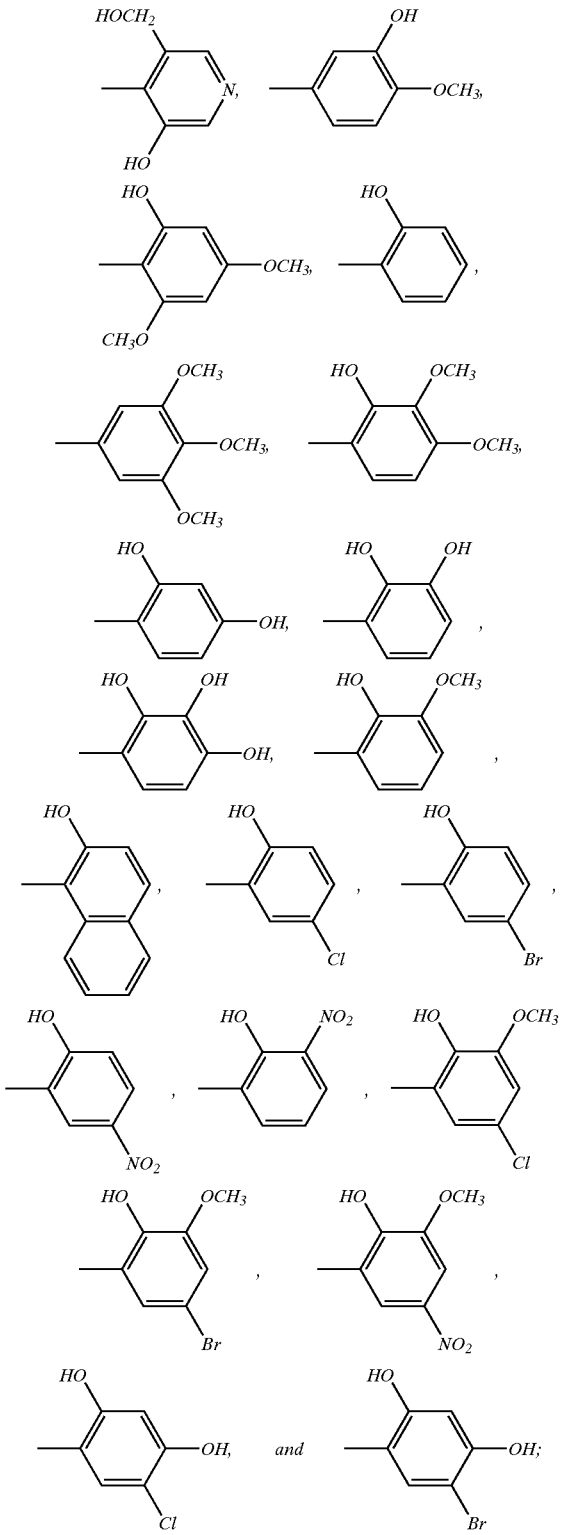

and R' is hydrogen.

12. A huperzine A compound of the formula

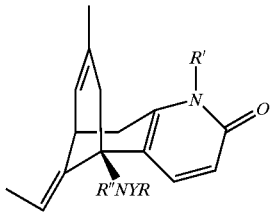

wherein

Y and —R" together form =CH; and

R is

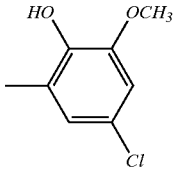

13. A huperzine A compound of the formula

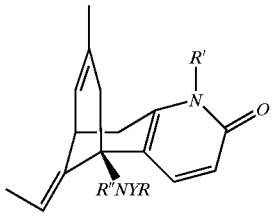

wherein

Y and —R" together form =CH; and

R is

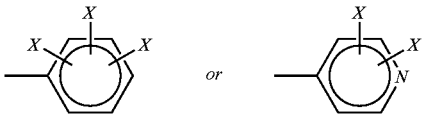

wherein each X is independently selected from the group consisting of hydrogen, methoxy, nitro, halogen, hydroxymethyl, and hydroxy;

and R' is H.

14. A method of treating amyasthenia by inhibiting cholinesterase comprising administering a huperzine A compound according to claim 11 to a patient in need of such treatment in an amount effective to inhibit cholinesterase.

15. A method of treating amyasthenia by inhibiting cholinesterase comprising administering a huperzine A compound according to claim 12 to a patient in need of such treatment in an amount effective to inhibit cholinesterase.

16. A method of treating amyasthenia by inhibiting cholinesterase comprising administering a huperzine A compound according to claim 13 to a patient in need of such treatment in an amount effective to inhibit cholinesterase.

17. A method of treating dysmnesia caused by a failure in central cholinergic system by inhibiting cholinesterase comprising administering a huperzine A compound according to claim 11 to a patient in need of such treatment in an amount effective to inhibit cholinesterase.

*18. A method of treatment dysmnesia caused by a failure in central cholinergic system by inhibiting cholinesterase comprising administering a huperzine A compound according to claim 12 to a patient in need of such treatment in an amount effective to inhibit cholinesterase.*

*19. A method of treating dysmnesia caused by a failure in central cholinergic system by inhibiting cholinesterase comprising administering a huperzine A compound according to claim 13 to a patient in need of such treatment in an amount effective to inhibit cholinesterase.*

*20. A method of inhibiting cholinesterase comprising administering a huperzine A compound according to claim 11 in an amount effective to inhibit colinesterase to a patient in need of such treatment.*

*21. A method of inhibiting cholinesterase comprising administering a huperzine A compound according to claim 12 in an amount effective to inhibit colinesterase to a patient in need of such treatment.*

*22. A method of inhibiting cholinesterase comprising administering a huperzine A compound according to claim 13 in an amount effective to inhibit colinesterase to a patient in need of such treatment.*

*23. A method of improving memory impairment comprising administering a huperzine A compound according to claim 11 in an amount effective to improve memory impairment to a patient in need of such treatment.*

*24. A method of improving memory impairment comprising administering a huperzine A compound according to claim 12 in an amount effective to improve memory impairment to a patient in need of such treatment.*

*25. A method of improving memory impairment comprising administering a huperzine A compound according to claim 13 in an amount effective to improve memory impairment to a patient in need of such treatment.*

* * * * *